(12) United States Patent
Mou et al.

(10) Patent No.: US 11,885,785 B2
(45) Date of Patent: *Jan. 30, 2024

(54) HEALTH MONITORING DEVICE HAVING GAS DETECTION FUNCTION

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Tsung-I Lin, Hsinchu (TW); Chang-Yen Tsai, Hsinchu (TW); Wei-Ming Lee, Hsinchu (TW)

(73) Assignee: Microjet Technology Co., Ltd., Hsinchu (TW)

( * ) Notice: Subject to any disclaimer, the term of this patent is extended or adjusted under 35 U.S.C. 154(b) by 593 days.

This patent is subject to a terminal disclaimer.

(21) Appl. No.: 17/036,688

(22) Filed: Sep. 29, 2020

(65) Prior Publication Data
US 2021/0208120 A1   Jul. 8, 2021

(30) Foreign Application Priority Data
Jan. 8, 2020   (TW) .................................. 109100666

(51) Int. Cl.
  *G01N 33/00*   (2006.01)
  *H10N 30/80*   (2023.01)
  *H10N 30/87*   (2023.01)
(52) U.S. Cl.
  CPC ..... *G01N 33/0027* (2013.01); *G01N 33/0063* (2013.01); *H10N 30/802* (2023.02); *H10N 30/87* (2023.02)

(58) Field of Classification Search
  CPC .... G01N 15/0205; G01N 15/02; G01N 15/04; G01N 2015/045; G01N 2015/03; G01N 2015/035; G01N 15/06; G01N 23/00; G01N 23/02; G01N 23/201; G01N 21/00; G01N 21/47; G01N 21/90; G01N 2223/00; G01N 15/1434; G01N 15/1436; G01N 2223/05;
  (Continued)

(56) References Cited

U.S. PATENT DOCUMENTS 9,728,063 B1 *  8/2017  Fu .......................... G08B 21/14
10,969,322 B2 *  4/2021  Mou .................. G01N 15/0637
(Continued)

FOREIGN PATENT DOCUMENTS

CN   2932374 Y   *  8/2007
CN   204129448 U  *  1/2015
(Continued)

*Primary Examiner* — John Fitzgerald
*Assistant Examiner* — Truong D Phan
(74) *Attorney, Agent, or Firm* — Birch, Stewart, Kolasch & Birch, LLP

(57) ABSTRACT

A health monitoring device having gas detection function is disclosed. The health monitoring device includes a main body. The main body has at least one inlet and at least one outlet, and includes a gas detection module. The gas detection module includes a piezoelectric actuator and at least one sensor. Gas is inhaled into the main body through the inlet by the piezoelectric actuator, is discharged out through the outlet, and is transported to the at least one sensor to be detected so as to obtain gas information.

12 Claims, 19 Drawing Sheets

(58) Field of Classification Search
CPC ....... G01N 2223/052; G01N 2223/051; G01N 2223/053; G01N 2291/015; G01N 23/20083; G01N 23/203; G01N 2021/4702; G01N 2021/4728; G01N 2021/555; G01N 2015/0238; G01N 15/0211
See application file for complete search history.

(56) References Cited

U.S. PATENT DOCUMENTS

| | | | |
|---|---|---|---|
| 11,543,397 B2 * | 1/2023 | Mou | G01N 33/0073 |
| 11,585,745 B2 * | 2/2023 | Mou | G01N 1/24 |
| 2019/0187035 A1 | 6/2019 | Mou et al. | |

FOREIGN PATENT DOCUMENTS

| | | | |
|---|---|---|---|
| CN | 110501455 A | | 11/2019 |
| TW | M58174 U | | 8/2019 |
| TW | 201942558 A | | 11/2019 |
| TW | I676788 B | | 11/2019 |
| WO | WO-2018076405 A1 * | | 5/2018 |

\* cited by examiner

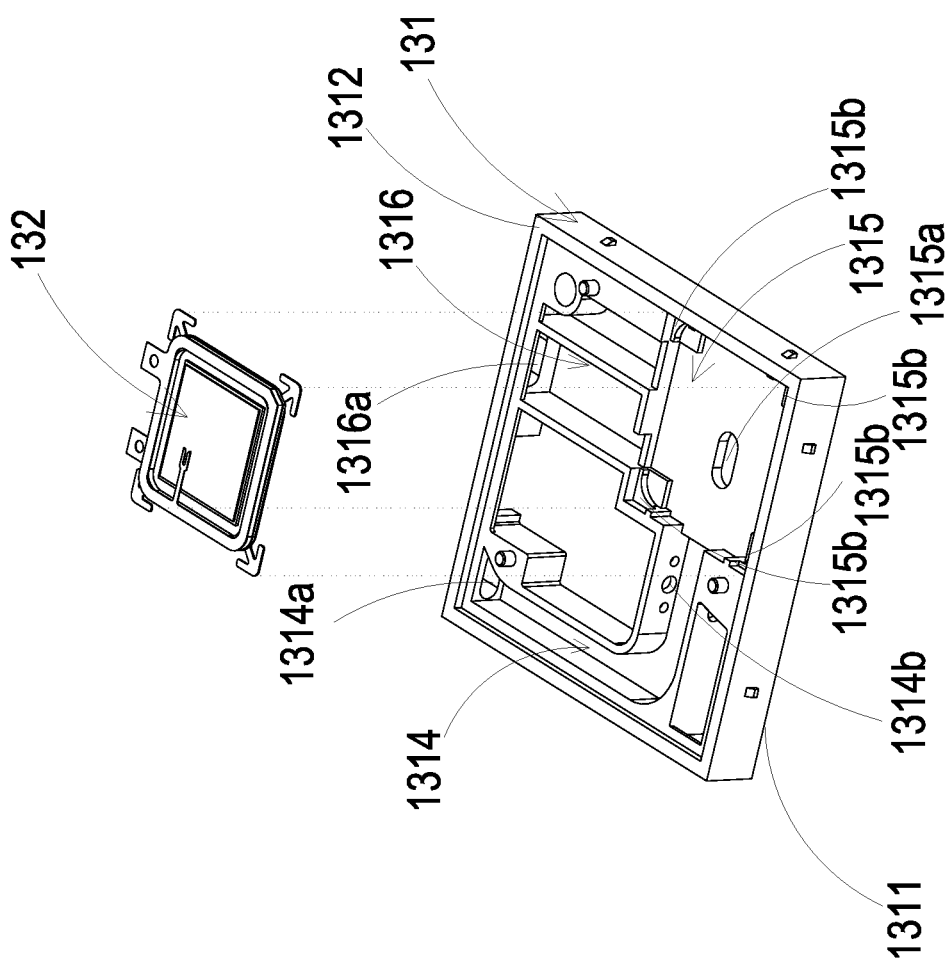

US 11,885,785 B2

HEALTH MONITORING DEVICE HAVING GAS DETECTION FUNCTION

FIELD OF THE INVENTION

The present disclosure relates to a health monitoring device having gas detection function, and more particularly to a health monitoring device having gas detection function to provide gas information.

BACKGROUND OF THE INVENTION

With the popularization of medical concepts, the concept of early detection or prevention is rising, so that people are paying more and more attention to daily body information testing, for example weight, body fat, blood pressure, heartbeat, sleep quality, etc. In addition, due to the increasing air pollution recently, in addition to their own health conditions, people pay more and more attention to the quality of the air around their lives. For example, carbon monoxide, carbon dioxide, volatile organic compounds (VOC), PM2.5, nitric oxide, sulfur monoxide and even the suspended particles contained in the air are exposed in the environment to affect the human health, and even endanger the life seriously. Therefore, the quality of environmental air has attracted the attention of various countries. At present, how to detect the air quality and avoid the harm is a problem that urgently needs to be solved.

In order to confirm the quality of the air, it is feasible to use a gas sensor to detect the air surrounding in the environment. If the detection information is provided in real time to warn the people in the environment, it is helpful of avoiding the harm and facilitates the people to escape the hazard immediately. Thus, it prevents the hazardous gas exposed in the environment from affecting the human health and causing the harm. Therefore, it is a very good application to use a gas sensor to detect the air in the surrounding environment. How to combine a health monitoring device and an air quality detection device for allowing the users to examine their own health conditions and monitor the air quality in real time is an important subject developed in the present disclosure.

SUMMARY OF THE INVENTION

An object of the present disclosure provides a health monitoring device having gas detection function. By using the health monitoring device, the air quality around the user is detected by the gas detection module at any time, and the users can not only examine their own health conditions but also confirm the air quality in the environment.

In accordance with an aspect of the present disclosure, a health monitoring device having gas detection function is provided. The health monitoring device includes a main body. The main body has at least one inlet and at least one outlet, and includes a gas detection module. The gas detection module includes a piezoelectric actuator and at least one sensor. Gas is inhaled into the main body through the inlet by the piezoelectric actuator, is discharged out through the outlet, and is transported to the at least one sensor to be detected so as to obtain gas information.

The above contents of the present disclosure will become more readily apparent to those ordinarily skilled in the art after reviewing the following detailed description and accompanying drawings, in which:

BRIEF DESCRIPTION OF THE DRAWINGS

FIG. 5A is a schematic exploded view illustrating the combination of the piezoelectric actuator and the base;

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
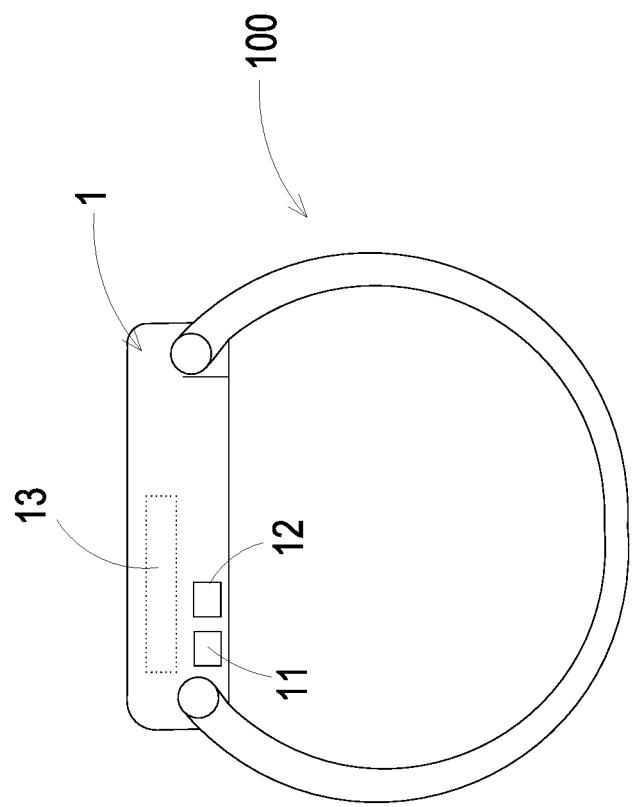
FIG. 1 shows a schematic exterior view illustrating a health monitoring device having gas detection function according to an embodiment of the present disclosure.

Please refer to FIG. 1. The present disclosure provides a health monitoring device 100 having gas detection function. The health monitoring device 100 is one selected from a group consisting of a sphygmomanometer, a smart watch, a smart bracelet, a weight scale, a thermometer, a sleep detection device, a buddha bead, an electronic nose, an odor measuring instrument, a gas analyzer, a wine measuring machine and a breathalyzer, and includes a main body 1. The main body 1 includes at least one inlet 11, at least one outlet 12 and a gas detection module 13. In this embodiment, the main body 1 has an inlet 11 and an outlet 12, but not limited thereto. The gas detection module 13 is disposed in the main body 1 to detect the gas within the main body 1 and obtain gas information.

Please refer to FIGS. 2A to 2C, 3A, 3B, 4, 5A and 5B. The gas detection module 13 includes a base 131, a piezoelectric actuator 132, a driving circuit board 133, a laser component 134, a particulate sensor 135 and an outer cover 136. In the embodiment, the base 131 includes a first surface 1311, a second surface 1312, a laser loading region 1313, a gas-inlet groove 1314, a gas-guiding-component loading region 1315, and a gas-outlet groove 1316. The first surface 1311 and the second surface 1312 are two opposite surfaces. The laser loading region 1313 is hollowed out from the first surface 1311 to the second surface 1312. The gas-inlet groove 1314 is concavely formed from the second surface 1312 and disposed adjacent to the laser loading region 1313. The gas-inlet groove 1314 includes a gas-inlet 1314a and two lateral walls. The gas-inlet 1314a is in fluid communication with an environment outside the base 131 and spatially corresponds to the inlet opening 1361a of the outer cover 136. The two lateral walls are disposed adjacent to the laser loading region 1313 and are penetrated by the transparent window 1314b. The transparent window 1314b is opened on the lateral wall and is in communication with the laser loading region 1313. In that, the first surface 1311 of the base 131 is attached and covered with the outer cover 136, and the second surface 1312 of the base 131 is attached and covered with the driving circuit board 133, so that an inlet path is collaboratively defined by the gas-inlet groove 1314 and the driving circuit board 133.

In the embodiment, the gas-guiding-component loading region 1315 is concavely formed from the second surface 1312 and in fluid communication with the gas-inlet groove 1314. A ventilation hole 1315a penetrates a bottom surface of the gas-guiding-component loading region 1315. The gas-outlet groove 1316 includes a gas-outlet 1316a, and the gas-outlet 1316a spatially corresponds to the outlet opening 1361b of the outer cover 136. The gas-outlet groove 1316 includes a first section 1316b and a second section 1316c. The first section 1316b is hollowed out from the first surface 1311 to the second surface 1312 in a vertical projection area of the gas-guiding-component loading region 1315 spatially corresponding thereto. The second section 1316c is hollowed out from the first surface 1311 to the second surface 1312 in a region where the first surface 1311 is not aligned with the vertical projection area of the gas-guiding-component loading region 1315 and extended therefrom. The first section 1316b and the second section 1316c are connected to form a stepped structure. Moreover, the first section 1316b of the gas-outlet groove 1316 is in fluid communication with the ventilation hole 1315a of the gas-guiding-component loading region 1315, and the second section 1316c of the gas-outlet groove 1316 is in fluid communication with the gas-outlet 1316a. In that, the first surface 1311 of the base 131 is attached and covered with the outer cover 136, and the second surface 1312 of the base 131 is attached and covered with the driving circuit board 133, so that an outlet path is collaboratively defined by the gas-outlet groove 1316, the outlet cover 136 and the driving circuit board 133.

Figure 4:
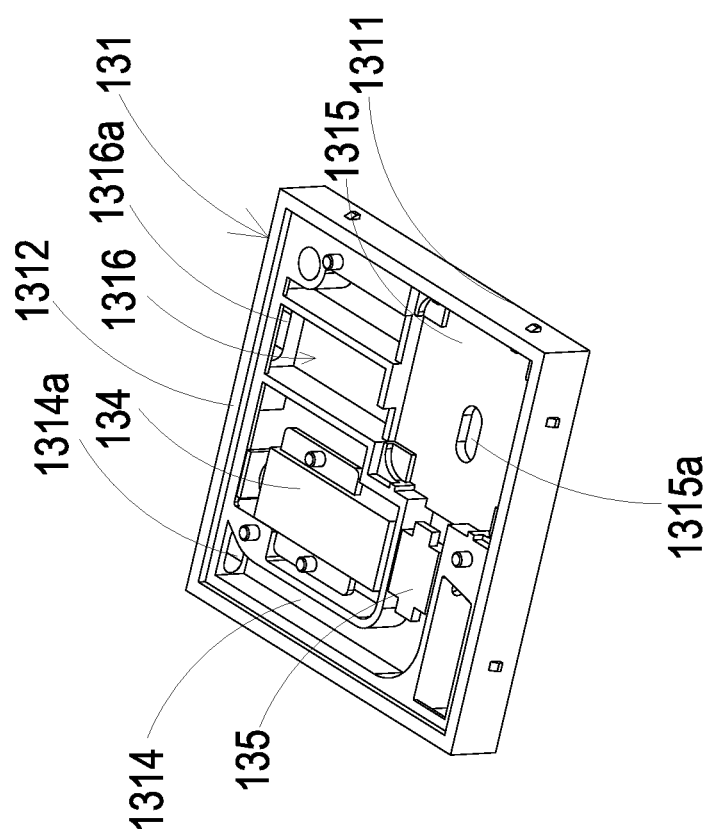
FIG. 4 is a schematic perspective view illustrating a laser component and a particulate sensor accommodated in the base of the present disclosure.

Please refer to FIG. 4. In the embodiment, the laser component 134 and the particulate sensor 135 are disposed on the driving circuit board 133 and accommodated in the base 131. In order to describe the positions of the laser component 134 and the particulate sensor 135 in the base 131, the driving circuit board 133 is specifically omitted in FIG. 4 to explain clearly. Please refer to FIG. 4 and FIG. 2C. The laser component 134 is accommodated in the laser loading region 1313 of the base 131, and the particulate sensor 135 is accommodated in the gas-inlet groove 1314 of the base 131 and aligned to the laser component 134. In addition, the laser component 134 spatially corresponds to the transparent window 1314b, a light beam emitted by the laser component 134 passes through the transparent window 1314b and is irradiated into the gas-inlet groove 1314. A light beam path emitted from the laser component 134 passes through the transparent window 1314b and extends in a direction perpendicular to the gas-inlet groove 1314, thereby forming an orthogonal direction with the gas-inlet groove 1314.

In the embodiment, a projecting light beam emitted from the laser component 134 passes through the transparent window 1314b and enters the gas-inlet groove 1314, and suspended particles contained in the gas passing through the gas-inlet groove 1314 is irradiated by the projecting light beam. When the suspended particles contained in the gas are irradiated to generate scattered light spots, the scattered light spots are received and calculated by the particulate sensor 135 for obtaining related information about the sizes and the concentration of the suspended particles contained in the gas. In the embodiment, the particulate sensor 135 is a PM2.5 sensor.

Figure 5B:
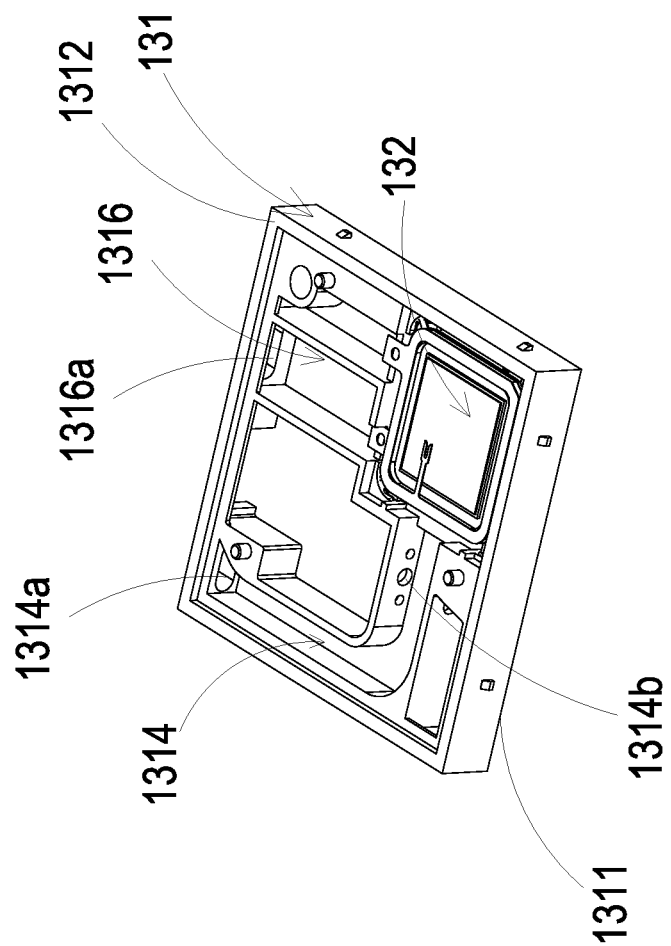
FIG. 5B is a schematic perspective view illustrating the combination of the piezoelectric actuator and the base.

Please refer to FIG. 5A and FIG. 5B. The piezoelectric actuator 132 is accommodated in the gas-guiding-component loading region 1315 of the base 131. Preferably but not exclusively, the gas-guiding-component loading region 1315 is square and includes four positioning notches 1315b disposed at four corners of the gas-guiding-component loading region 1315, respectively. The piezoelectric actuator 132 is disposed in the gas-guiding-component loading region 1315 through the four positioning notches 1315b. In addition, the gas-guiding-component loading region 1315 is in fluid communication with the gas-inlet groove 1314. When the piezoelectric actuator 132 is enabled, the gas in the gas-inlet groove 1314 is inhaled by the piezoelectric actuator 132, so that the gas flows into the piezoelectric actuator 132. Furthermore, the gas is transported into the gas-outlet groove 1316 through the ventilation hole 1315a of the gas-guiding-component loading region 1315. Moreover, by the actions of the piezoelectric actuator 132, the gas outside the main body 1 is inhaled into the main body 1 through the inlet 11, flows through the gas detection module 13, and finally is discharged out through the outlet 12 and guided to the particulate sensor 135 to be detected and obtain gas information.

Figure 2A:
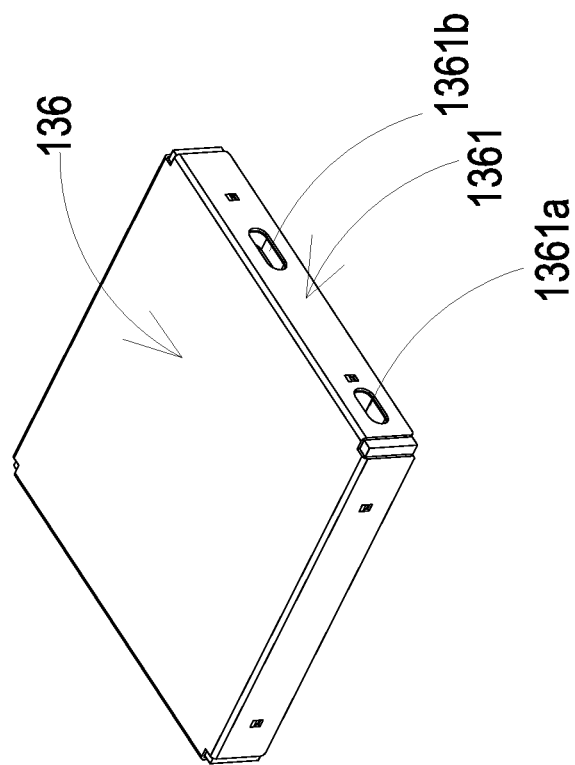
FIG. 2A is a schematic exterior view illustrating a gas detection module according to an embodiment of the present disclosure.
Figure 2B:
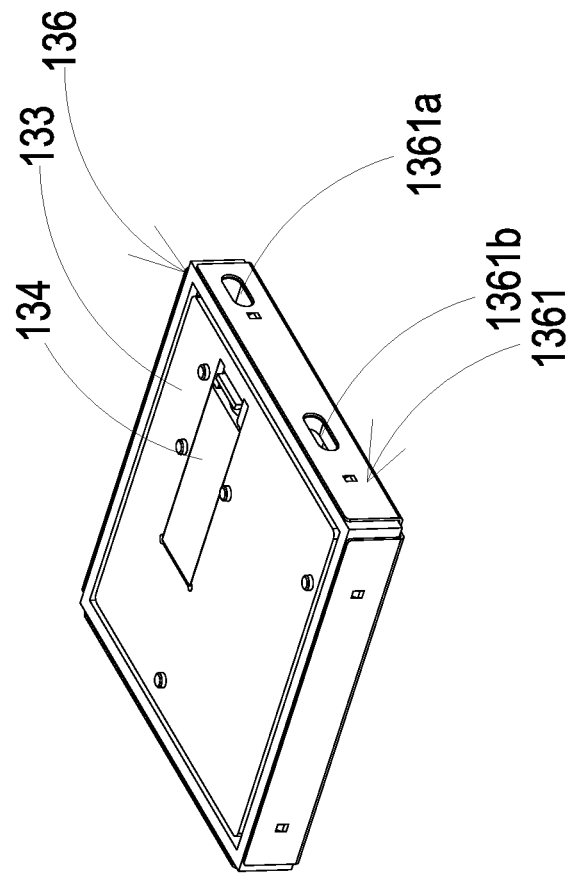
FIG. 2B is a schematic exterior view illustrating the gas detection module according to the embodiment of the present disclosure and taken from another perspective angle.
Figure 2C:
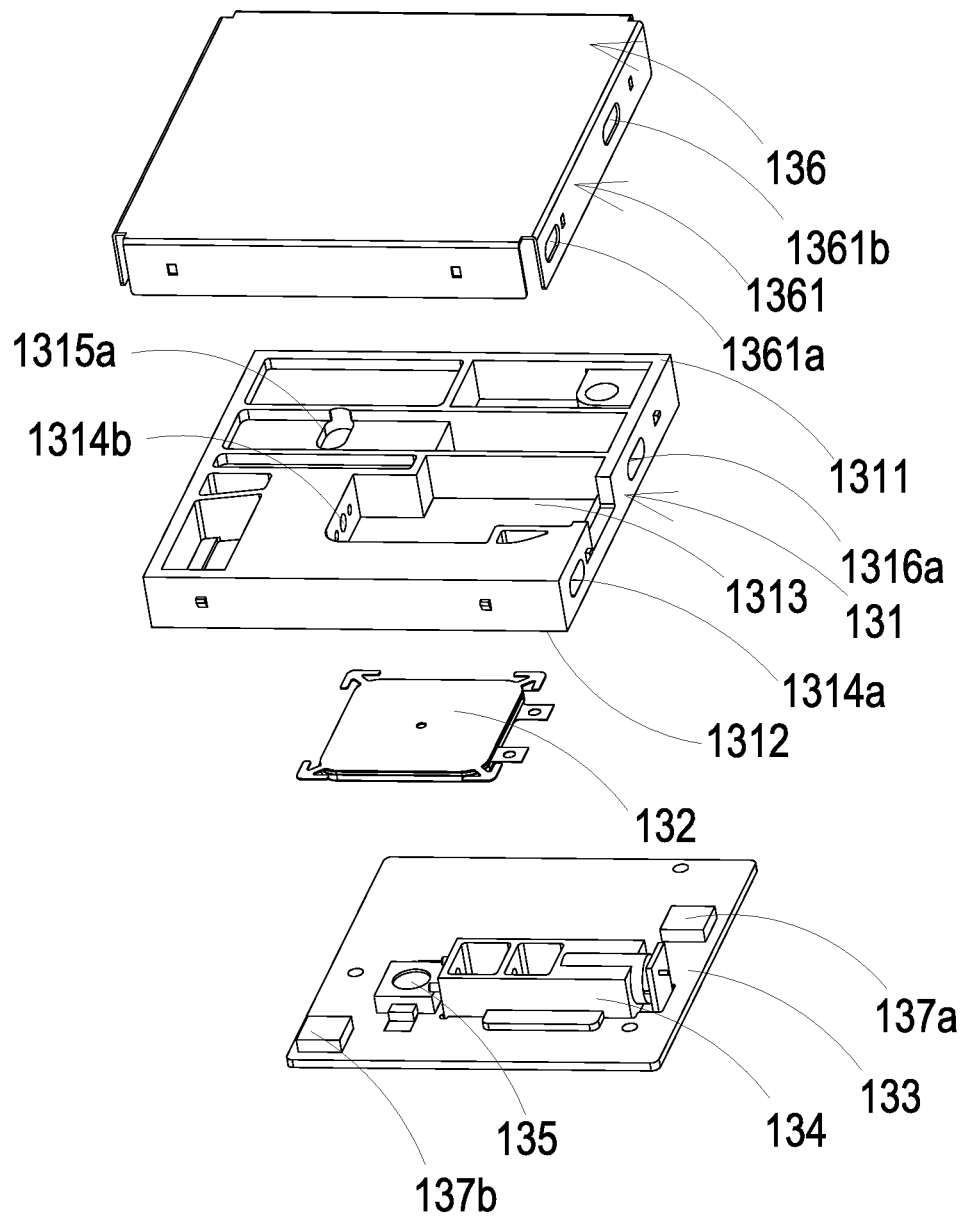
FIG. 2C is a schematic exploded view illustrating the gas detection module of the present disclosure.
Figure 3A:
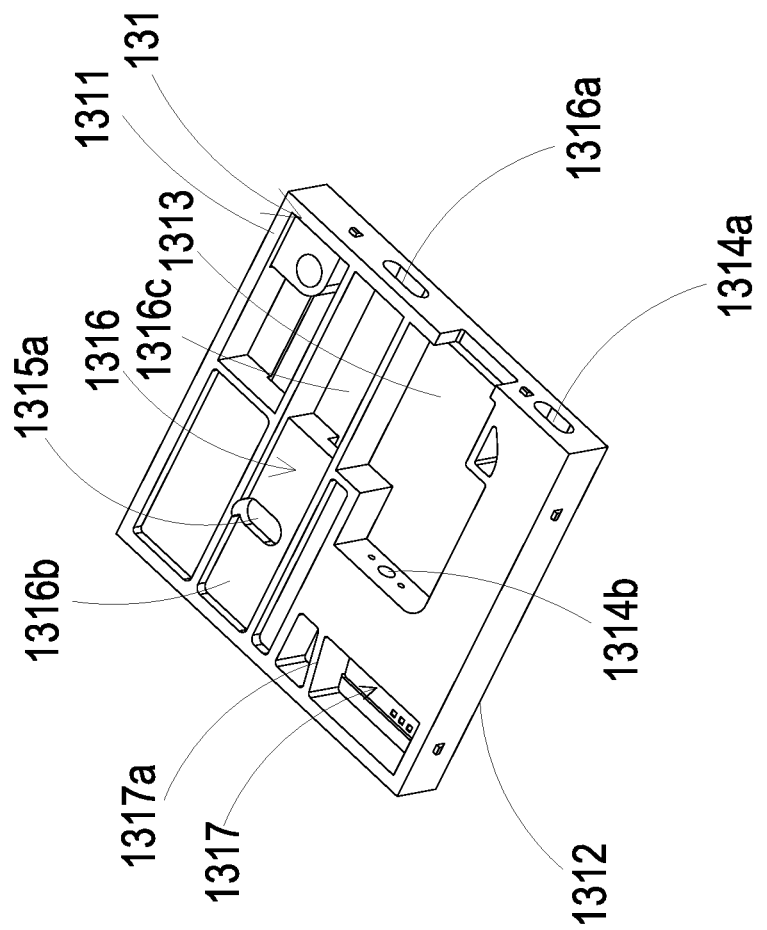
FIG. 3A is a schematic perspective view illustrating a base of the gas detection module of the present disclosure.
Figure 3B:
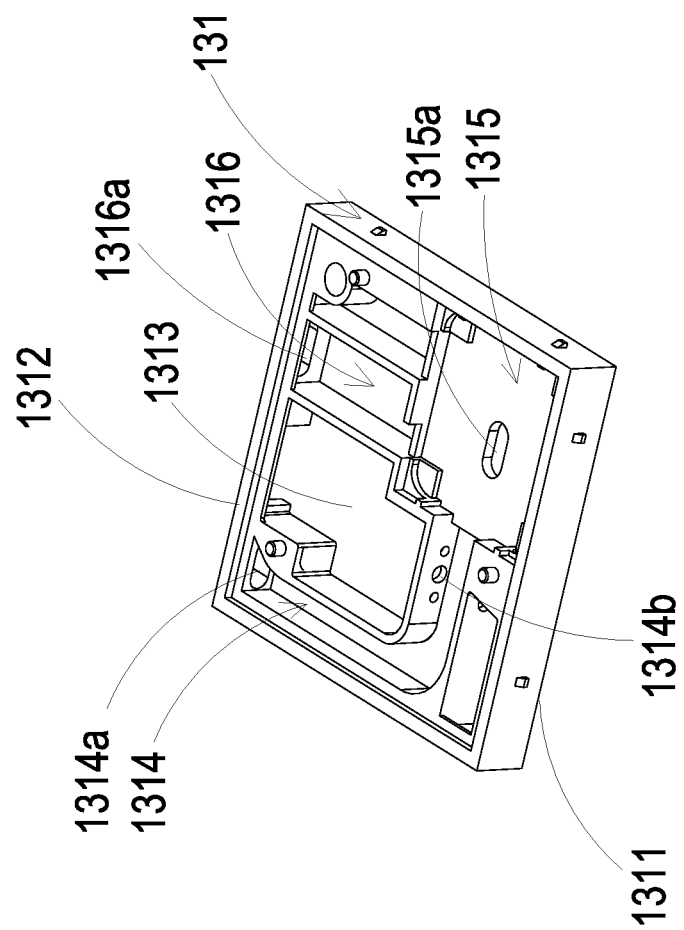
FIG. 3B is a schematic perspective view illustrating the base of the gas detection module of the present disclosure and taken from another perspective angle.

In the embodiment, the driving circuit board 133 covers and is attached to the second surface 1312 of the base 131 (as shown in FIG. 2C), and the laser component 134 is positioned and disposed on the driving circuit board 133, and is electrically connected to the driving circuit board 133. The particulate sensor 135 is positioned and disposed on the driving circuit board 133, and is electrically connected to the driving circuit board 133. The outer cover 136 covers the base 131 and is attached to the first surface 1311 of the base 131. Moreover, the outer cover 136 includes a side plate 1361. The side plate 1361 includes an inlet opening 1361a and an outlet opening 1361b. When outer cover 136 covers the base 131, the inlet opening 1361a is corresponding in position to the gas-inlet 1314a of the base 131, and the outlet opening 1361b is corresponding in position to the gas-outlet 1316a of the base 131.

Figure 6A:
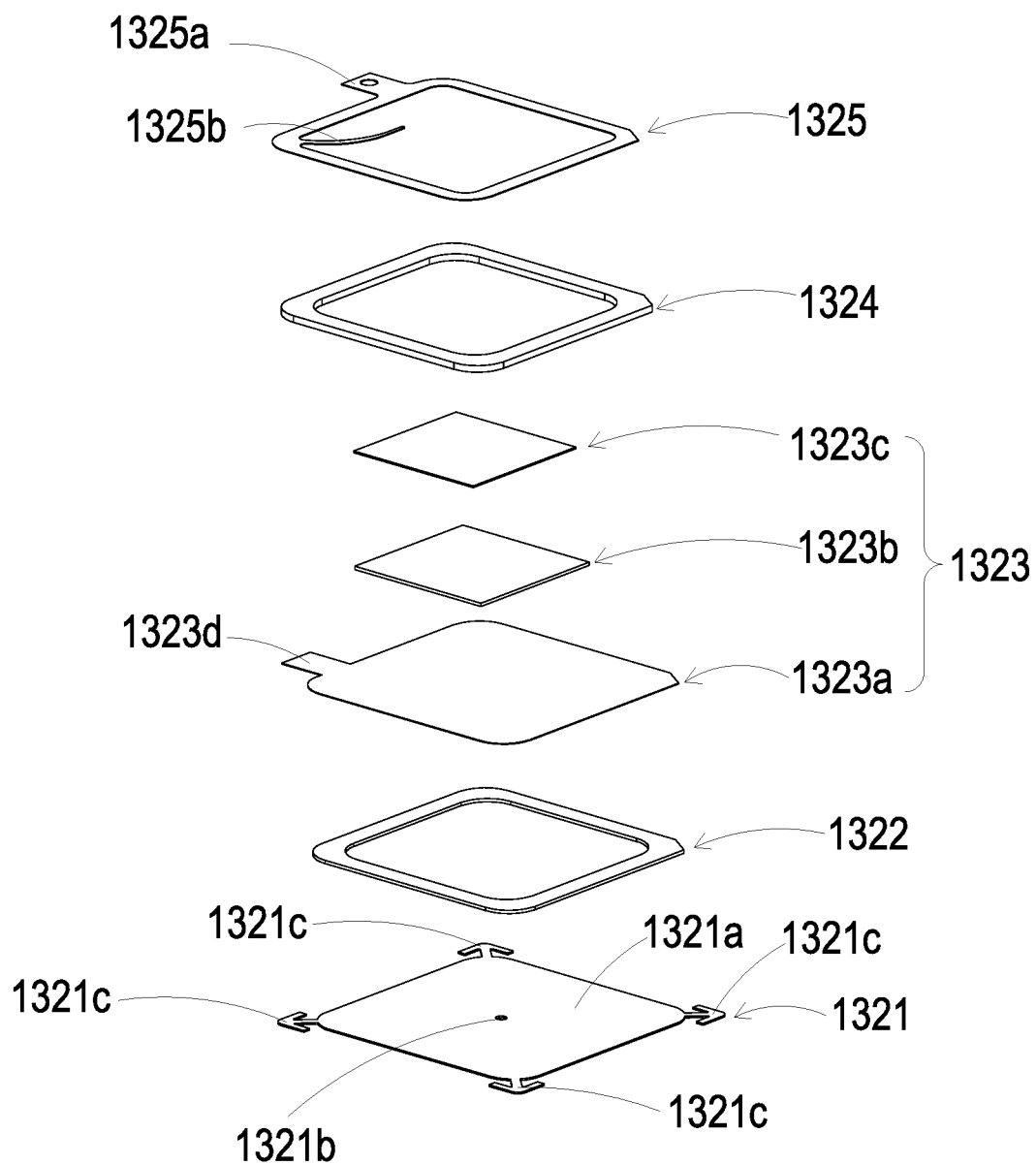
FIG. 6A is a schematic exploded view illustrating the piezoelectric actuator.
Figure 6B:
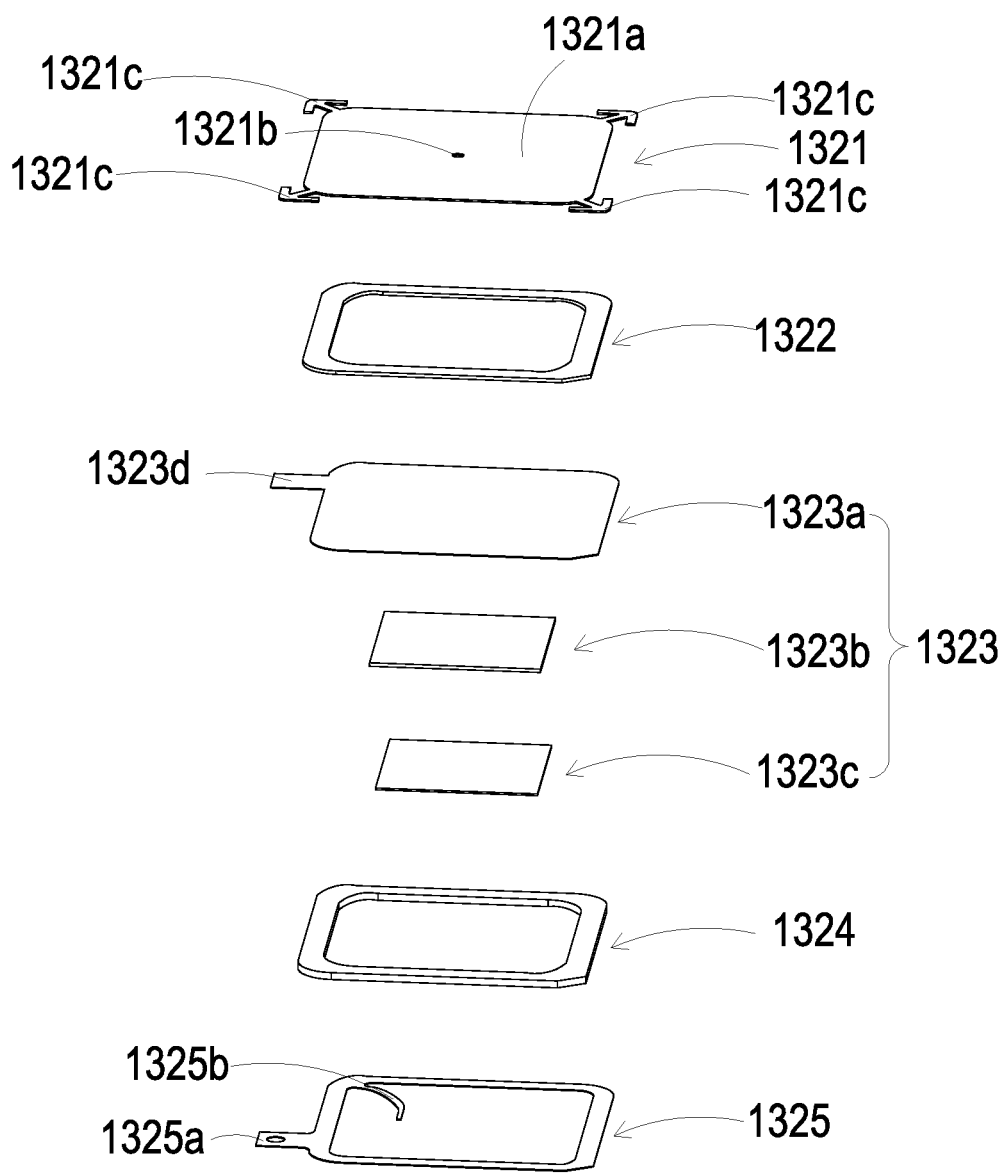
FIG. 6B is a schematic exploded view illustrating the piezoelectric actuator and taken from another perspective angle.

Please refer to FIGS. 6A and 6B. In the embodiment, the piezoelectric actuator 132 includes a gas-injection plate 1321, a chamber frame 1322, an actuator element 1323, an insulation frame 1324 and a conductive frame 1325.

In the embodiment, the gas-injection plate 1321 is made by a flexible material and includes a suspension plate 1321a, a hollow aperture 1321b and a plurality of connecting elements 1321c. The suspension plate 1321a is a sheet structure and permitted to undergo a bending deformation. Preferably but not exclusively, the shape and the size of the suspension plate 1321a are corresponding to an inner edge of the gas-guiding-component loading region 1315. The shape of the suspension plate 1321a is one selected from the group consisting of a square, a circle, an ellipse, a triangle and a polygon. The hollow aperture 1321b passes through a center of the suspension plate 1321a, so as to allow the gas to flow through. In the embodiment, there are four connecting elements 1321c. Preferably but not exclusively, the number and the type of the connecting elements 1321c mainly correspond to the positioning notches 1315b of the gas-guiding-component loading region 1315. Each connecting element 1321c and the corresponding positioning notch 1315b form an engagement structure, and are mutually engaged and fixed. Thus, the piezoelectric actuator 132 is disposed in the gas-guiding-component loading region 1315.

The chamber frame 1322 is carried and stacked on the gas-injection plate 1321. In addition, the shape of the chamber frame 1322 is corresponding to the gas-injection plate 1321. The actuator element 1323 is carried and stacked on the chamber frame 1322. A resonance chamber 1326 is collaboratively defined by the actuator element 1323, the chamber frame 1322 and the suspension plate 1321a and formed among the actuator element 1323, the chamber frame 1322 and the suspension plate 1321a. The insulation frame 1324 is carried and stacked on the actuator element 1323 and the appearance of the insulation frame 1324 is similar to that of the chamber frame 1322. The conductive frame 1325 is carried and stacked on the insulation frame 1324, and the appearance of the conductive frame 1325 is similar to that of the insulation frame 1324. In addition, the conductive frame 1325 includes a conducting pin 1325a and a conducting electrode 1325b. The conducting pin 1325a is extended outwardly from an outer edge of the conductive frame 1325, and the conducting electrode 1325b is extended inwardly from an inner edge of the conductive frame 1325. Moreover, the actuator element 1323 further includes a piezoelectric carrying plate 1323a, an adjusting resonance plate 1323b and a piezoelectric plate 1323c. The piezoelectric carrying plate 1323a is carried and stacked on the chamber frame 1322. The adjusting resonance plate 1323b is carried and stacked on the piezoelectric carrying plate 1323a. The piezoelectric plate 1323c is carried and stacked on the adjusting resonance plate 1323b. The adjusting resonance plate 1323b and the piezoelectric plate 1323c are accommodated in the insulation frame 1324. The conducting electrode 1325b of the conductive frame 1325 is electrically connected to the piezoelectric plate 1323c. In the embodiment, the piezoelectric carrying plate 1323a and the adjusting resonance plate 1323b are made by a conductive material. The piezoelectric carrying plate 1323a includes a piezoelectric pin 1323d. The piezoelectric pin 1323d and the conducting pin 1325a are electrically connected to a driving circuit (not shown) of the driving circuit board 133, so as to receive a driving signal, such as a driving frequency and a driving voltage. In that, a loop is formed by the piezoelectric pin 1323d, the piezoelectric carrying plate 1323a, the adjusting resonance plate 1323b, the piezoelectric plate 1323c, the conducting electrode 1325b, the conductive frame 1325 and the conducting pin 1325a for the driving signal. Moreover, the insulation frame 1324 is insulated between the conductive frame 1325 and the actuator element 1323, so as to avoid the occurrence of a short circuit. Thereby, the driving signal is transmitted to the piezoelectric plate 1323c. After receiving the driving signal such as the driving frequency and the driving voltage, the piezoelectric plate 1323c deforms due to the piezoelectric effect, and the piezoelectric carrying plate 1323a and the adjusting resonance plate 1323b are further driven to generate the bending deformation in the reciprocating manner.

As described above, the adjusting resonance plate 1323b is located between the piezoelectric plate 1323c and the piezoelectric carrying plate 1323a and served as a buffer between the piezoelectric plate 1323c and the piezoelectric carrying plate 1323a. Thereby, the vibration frequency of the piezoelectric carrying plate 1323a is adjustable. Basically, the thickness of the adjusting resonance plate 1323b is greater than the thickness of the piezoelectric carrying plate 1323a, and the thickness of the adjusting resonance plate 1323b is adjustable, thereby adjusting the vibration frequency of the actuator element 1323.

Please refer to FIGS. 6A to 6C and FIG. 7A. In the embodiment, the plurality of connecting elements 1321c are connected between the suspension plate 1321a and an inner edge of the gas-guiding-component loading region 1315 to define a plurality of vacant spaces 1321d for gas flowing. Please refer to FIG. 7A. The gas-injection plate 1321, the chamber frame 1322, the actuator element 1323, the insulation frame 1324 and the conductive frame 1325 are stacked and positioned in the gas-guiding-component loading region 1315 sequentially. A flowing chamber 1327 is formed between the gas-injection plate 1321 and the bottom surface (not shown) of the gas-guiding-component loading region 1315. The flowing chamber 1327 is in fluid communication with the resonance chamber 1326 among the actuator element 1323, the chamber frame 1322 and the suspension plate 1321a through the hollow aperture 1321b of the gas-injection plate 1321. By controlling the vibration frequency of the gas in the resonance chamber 1326 to be close to the vibration frequency of the suspension plate 1321a, the Helmholtz resonance effect is generated between the resonance chamber 1326 and the suspension plate 1321a, and thereby the efficiency of gas transportation is improved.

Figure 7A:
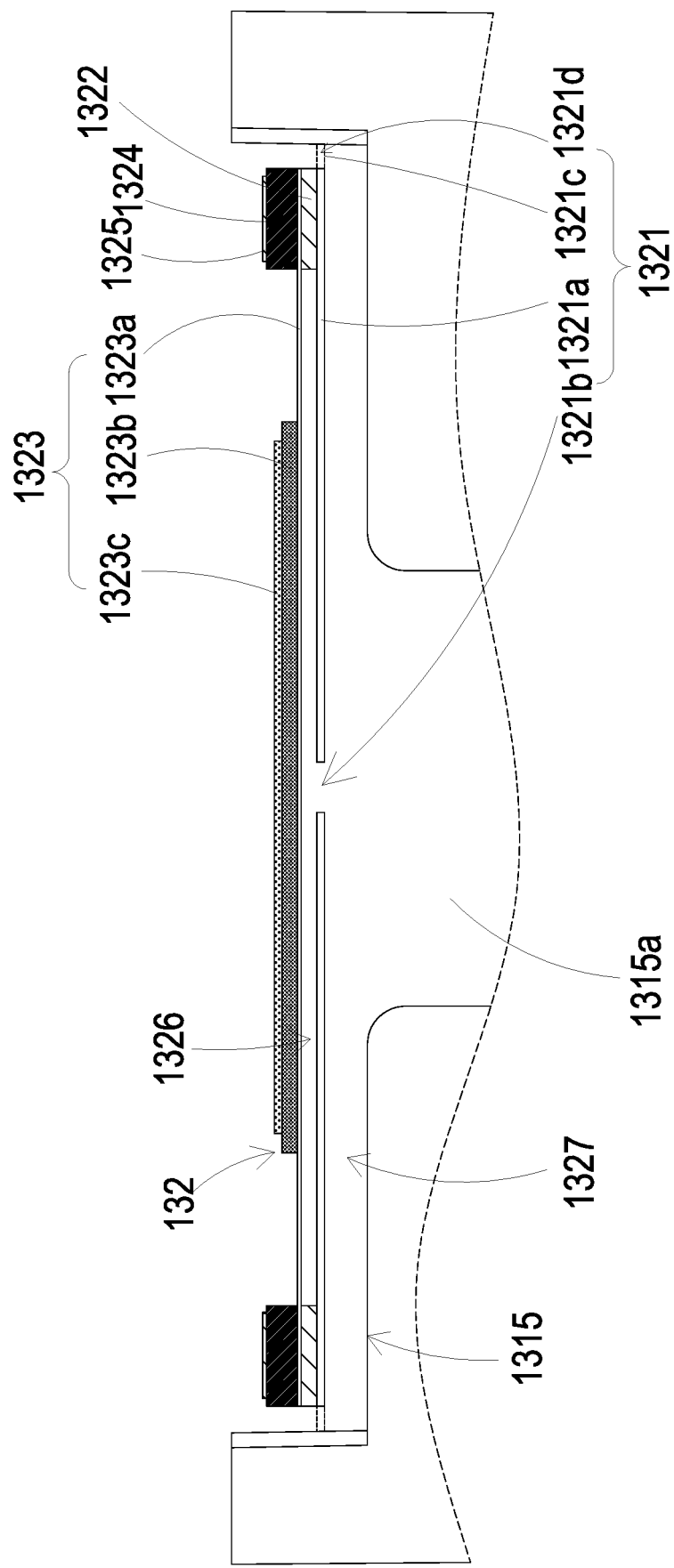
FIG. 7A is a schematic cross-sectional view illustrating the piezoelectric actuator accommodated in the gas-guiding-component loading region.
Figure 7B:
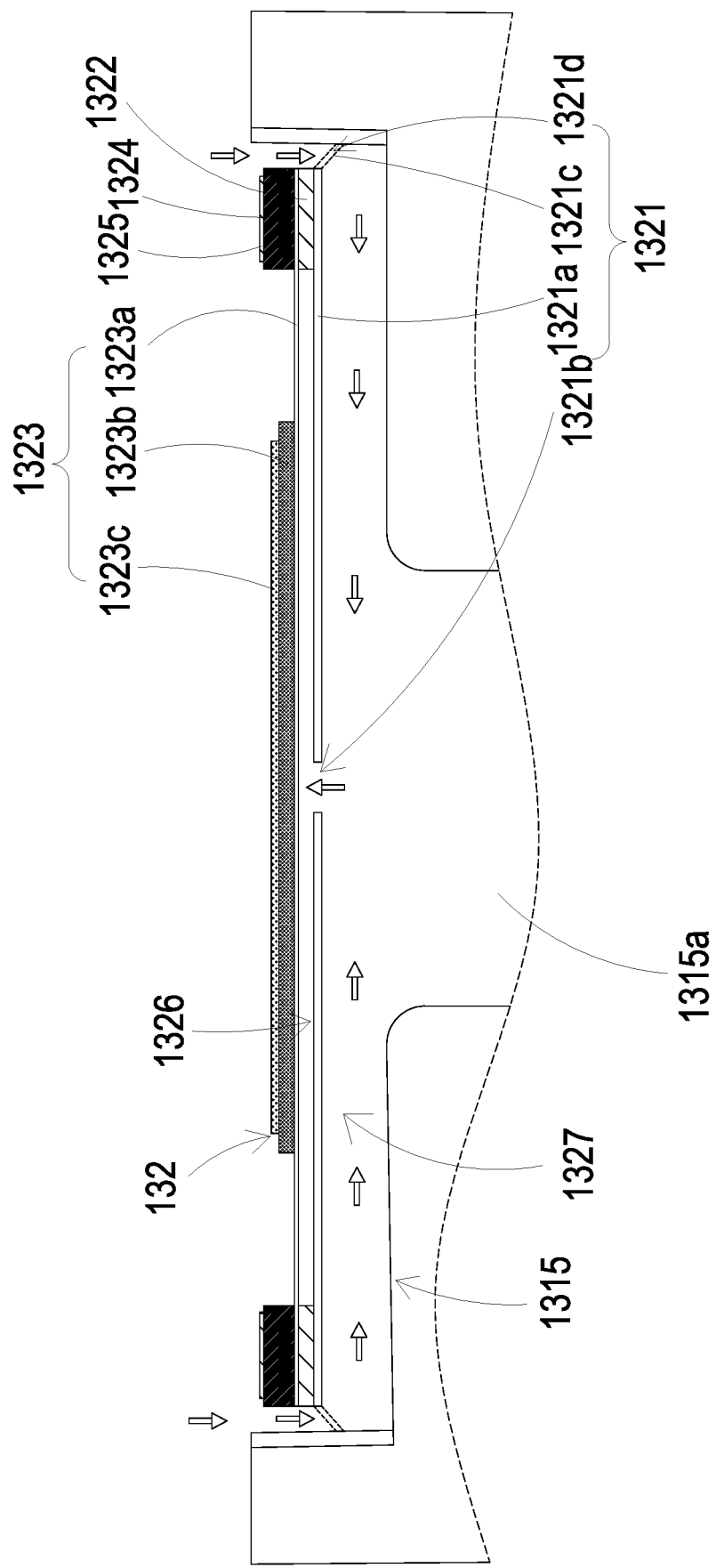
FIGS. 7B and 7C schematically illustrate the actions of the piezoelectric actuator of FIG. 7A.
Figure 7C:
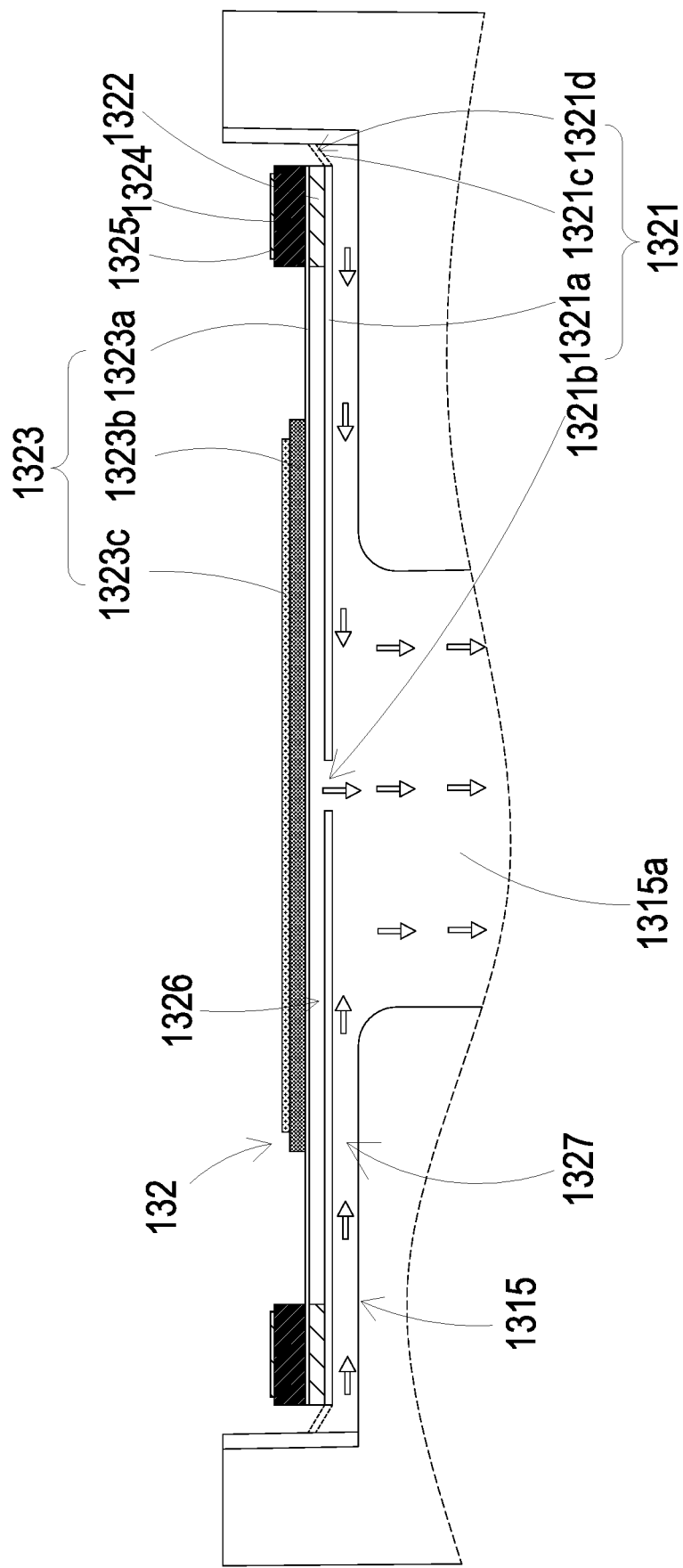

FIGS. 7B and 7C schematically illustrate the actions of the piezoelectric actuator of FIG. 7A. Please refer to FIG. 7B. When the piezoelectric plate 1323c is moved away from the bottom surface of the gas-guiding-component loading region 1315, the suspension plate 1321a of the gas-injection plate 1321 is moved away from the bottom surface of the gas-guiding-component loading region 1315. In that, the volume of the flowing chamber 1327 is expanded rapidly, the internal pressure of the flowing chamber 1327 is decreased to form a negative pressure, and the gas outside the piezoelectric actuator 132 is inhaled through the vacant spaces 1321d and enters the resonance chamber 1326 through the hollow aperture 1321b. Consequently, the pressure in the resonance chamber 1326 is increased to generate a pressure gradient. Further as shown in FIG. 7C, when the suspension plate 1321a of the gas-injection plate 1321 is driven by the piezoelectric plate 1323c to move towards the bottom surface of the gas-guiding-component loading region 1315, the gas in the resonance chamber 1326 is discharged out rapidly through the hollow aperture 1321b, and the gas in the flowing chamber 1327 is compressed. In that, the converged gas close to an ideal gas state of the Benulli's law is quickly and massively ejected out of the flowing chamber 1327. Moreover, according to the principle of inertia, since the gas pressure inside the resonance chamber 1326 after exhausting is lower than the equilibrium gas pressure, the gas is introduced into the resonance chamber 1326 again. By repeating the above actions shown in FIG. 7B and FIG. 7C, the piezoelectric plate 1323*c* is driven to generate the bending deformation in a reciprocating manner. Moreover, the vibration frequency of the gas in the resonance chamber 1326 is controlled to be close to the vibration frequency of the piezoelectric plate 1323*c*, so as to generate the Helmholtz resonance effect to achieve the gas transportation at high speed and in large quantities.

Figure 8A:
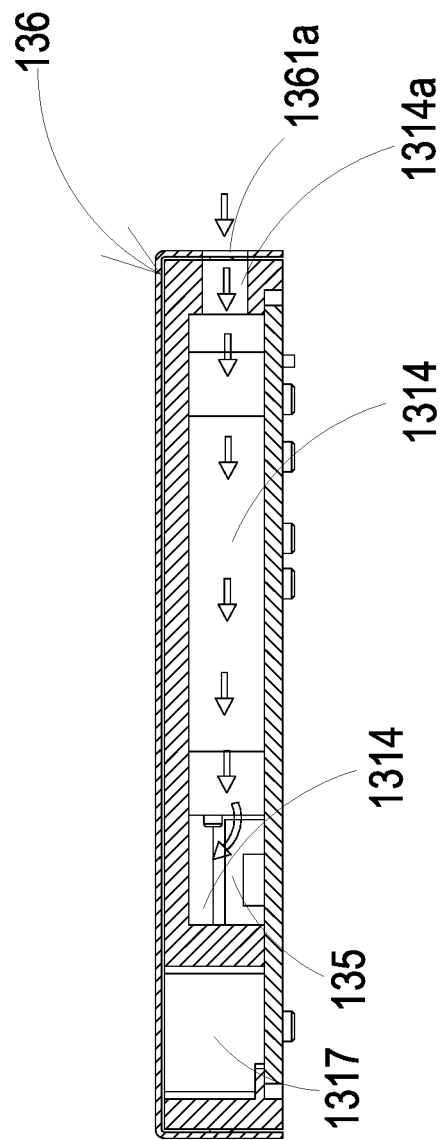
FIGS. 8A to 8C schematically illustrate gas flowing paths of the gas detection module.
Figure 8B:
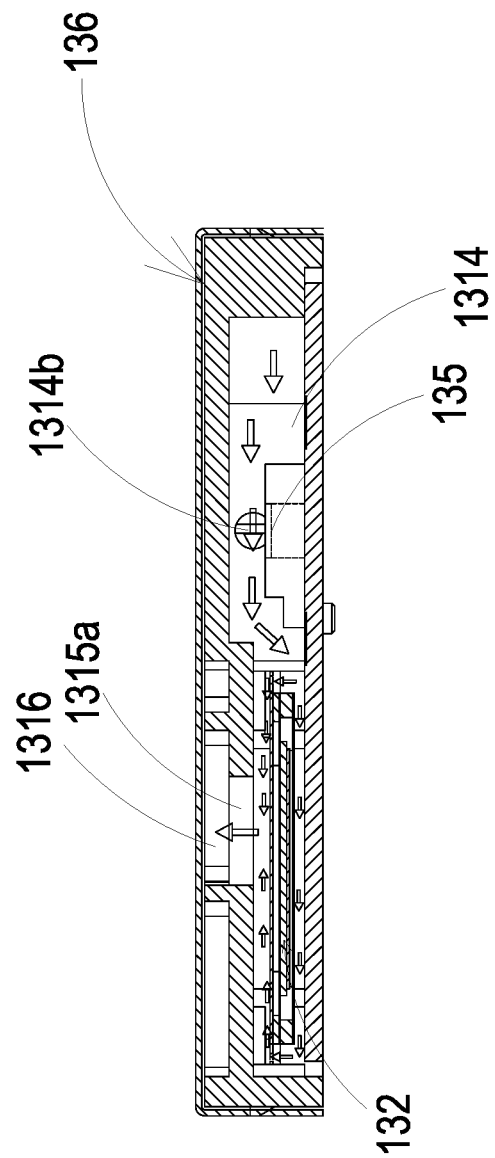
Figure 8C:
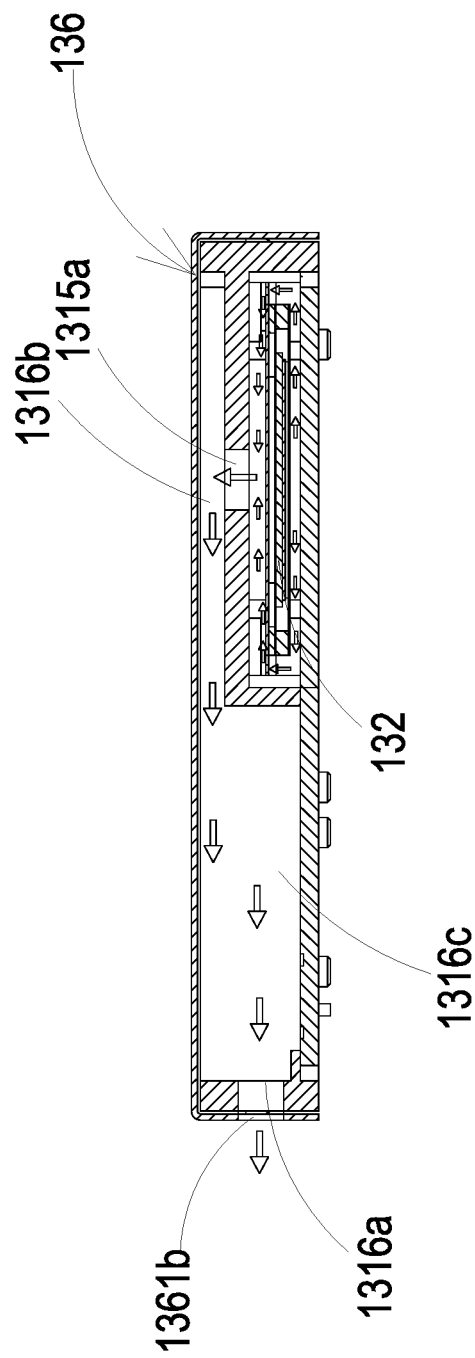

Please refer to FIGS. 8A to 8C. FIGS. 8A to 8C schematically illustrate gas flowing paths of the gas detection module. Firstly, as shown in FIG. 8A, the gas is inhaled through the inlet opening 1361*a* of the outer cover 136, flows into the gas-inlet groove 1314 of the base 131 through the gas-inlet 1314*a*, and is transported to the position of the particulate sensor 135. Further as shown in FIG. 8B, the piezoelectric actuator 132 is enabled continuously to inhale the gas in the inlet path, and it facilitates the gas to be introduced rapidly, flow stably, and be transported above the particulate sensor 135. At this time, a projecting light beam emitted from the laser component 134 passes through the transparent window 1314*b* to irritate the suspended particles contained in the gas flowing above the particulate sensor 135 in the gas-inlet groove 1314. When the suspended particles contained in the gas are irradiated to generate scattered light spots, the scattered light spots are received and calculated by the particulate sensor 135 for obtaining related information about the sizes and the concentration of the suspended particles contained in the gas. Moreover, the gas above the particulate sensor 135 is continuously driven and transported by the piezoelectric actuator 132, flows into the ventilation hole 1315*a* of the gas-guiding-component loading region 1315, and is transported to the first section 1316*b* of the gas-outlet groove 1316. As shown in FIG. 8C, after the gas flows into the first section 1316*b* of the gas-outlet groove 1316, the gas is continuously transported into the first section 1316*b* by the piezoelectric actuator 132, and the gas in the first section 1316*b* is pushed to the second section 1316*c*. Finally, the gas is discharged out through the gas-outlet 1316*a* and the outlet opening 1361*b*.

Figure 9:
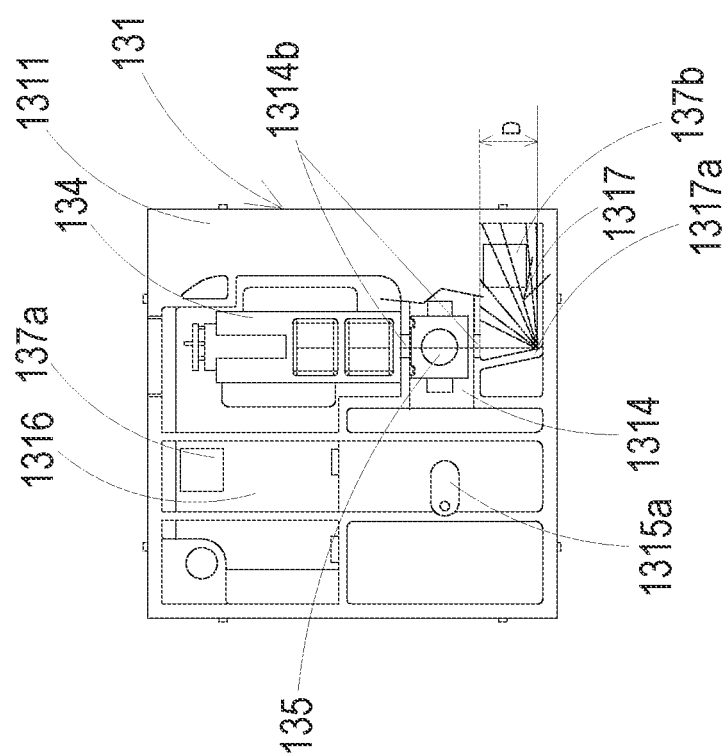
FIG. 9 schematically illustrates a light beam path emitted from the laser component.

As shown in FIG. 9, the base 131 further includes a light trapping region 1317. The light trapping region 1317 is hollowed out from the first surface 1311 to the second surface 1312 and spatially corresponds to the laser loading region 1313. In the embodiment, the light trapping region 1317 is corresponding to the transparent window 1314*b* so that the light beam emitted by the laser component 134 is projected into the light trapping region 1317. The light trapping region 1317 includes a light trapping structure 1317*a* having an oblique cone surface. The light trapping structure 1317*a* spatially corresponds to the light beam path emitted from the laser component 134. In addition, the projecting light beam emitted from the laser component 134 is reflected into the light trapping region 1317 through the oblique cone surface of the light trapping structure 1317*a*. It prevents the projecting light beam from being reflected to the position of the particulate sensor 135. In the embodiment, a light trapping distance D is maintained between the transparent window 1314*b* and a position where the light trapping structure 1317*a* receives the projecting light beam. Preferably but not exclusively, the light trapping distance D is greater than 3 mm. When the light trapping distance D is less than 3 mm, the projecting light beam projected on the light trapping structure 1317*a* is easy to be reflected back to the position of the particulate sensor 135 directly due to excessive stray light generated after reflection, and it results in distortion of detection accuracy.

Please refer to FIG. 2C and FIG. 9. The gas detection module 13 of the present disclosure is not only utilized to detect the suspended particles in the gas, but also further utilized to detect the characteristics of the introduced gas. For example, the gas is one selected form the group consisting of formaldehyde, ammonia, carbon monoxide, carbon dioxide, oxygen and ozone. In the embodiment, the gas detection module 13 further includes a first volatile-organic-compound sensor 137*a*. The first volatile-organic-compound sensor 137*a* is positioned and disposed on the driving circuit board 133, electrically connected to the driving circuit board 133, and accommodated in the gas-outlet groove 1316, so as to detect the gas flowing through the outlet path of the gas-outlet groove 1316. Thus, the concentration or characteristics of volatile organic compounds contained in the gas in the outlet path is detected. In the embodiment, the gas detection module 13 further includes a second volatile-organic-compound sensor 137*b*. The second volatile-organic-compound sensor 137*b* is positioned and disposed on the driving circuit board 133, and electrically connected to the driving circuit board 133. In the embodiment, the second volatile-organic-compound sensor 137*b* is accommodated in the light trapping region 1317. Thus, the concentration or characteristics of volatile organic compounds contained in the gas flowing through the inlet path of the gas-inlet groove 1314 and transported into the light trapping region 1317 through the transparent window 1314*b* is detected.

Figure 10:
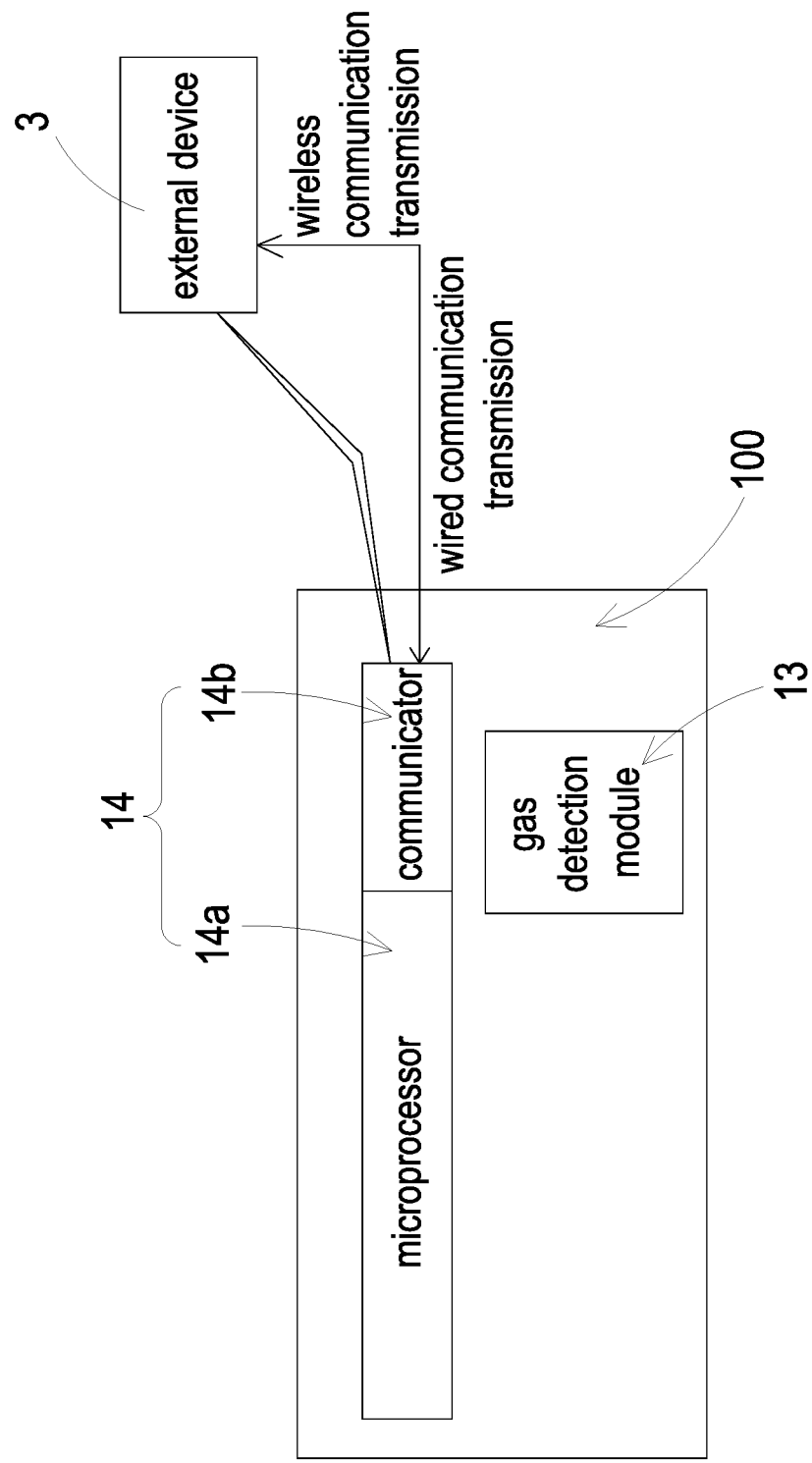
FIG. 10 is a block diagram showing the relationship between the controlling circuit unit and the related arrangement of the health monitoring device having gas detection function according to the embodiment of the present disclosure.

Please refer to FIGS. 2 and 10 again. In the embodiment, the health monitoring device 100 further includes a controlling circuit unit 14. The controlling circuit unit 14 includes a microprocessor 14*a* and a communicator 14*b*. The gas detection module 13 is electrically connected to the controlling circuit unit 14. The microprocessor 14*a* enables the gas detection module 13 to detect and operate by controlling a driving signal of the gas detection module 13, and converts a detection raw data of the gas detection module 13 into a detection data for storing. In addition, the microprocessor 14*a* enables the piezoelectric actuator 132 to operate by controlling a driving signal of the piezoelectric actuator 132, and controls the operation of the health monitoring device 100 according to the detection data. The communicator 14*b* receives the detection data outputted by the microprocessor 14*a*, and allows the detection data to be externally transmitted to an external device 3 through the communication transmission for storing, so that the external device 3 generates a gas detection information and an alarm. Preferably but not exclusively, the above-mentioned external device 3 is one selected from the group consisting of a cloud system, a portable device and a computer system. Preferably but not exclusively, the communication transmission is the wired communication transmission, such as USB connection transmission. Preferably but not exclusively, the communication transmission is the wireless communication transmission, such as Wi-Fi transmission, Bluetooth transmission, a radio frequency identification transmission or a near field communication transmission.

From the above descriptions, the present disclosure provides a health monitoring device. The health monitoring device can not only allow the user to examine their own health conditions at any time, for example weight, body fat, blood pressure, heartbeat, or sleep quality, but also provide gas information around the user for allowing the user to obtain the air quality in the surrounding environment. In addition to human body information, the environment information is provided to warn the user in the environment, so as to avoid the harm and facilitate the user to escape the hazard immediately. The present disclosure includes the industrial applicability.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A health monitoring device having gas detection function and allowing users to examine their own health conditions at any time, wherein the health conditions are weight, body fat, blood pressure, heartbeat, or sleep quality, and the health monitoring device comprises:
 a main body having at least one inlet, at least one outlet and a gas detection module, wherein the gas detection module comprises a piezoelectric actuator and at least one sensor, wherein gas is inhaled into the main body through the inlet by the piezoelectric actuator, is discharged out through the outlet, and is transported to the at least one sensor to be detected so as to obtain gas information, wherein the piezoelectric actuator comprises:
 a gas-injection plate comprising a plurality of connecting elements, a suspension plate and a hollow aperture, wherein the suspension plate is permitted to undergo a bending deformation, the plurality of connecting elements are adjacent to a periphery of the suspension plate, and the hollow aperture is formed at a center of the suspension plate, wherein the suspension plate is fixed through the plurality of connecting elements, and the plurality of connecting elements are configured for elastically supporting the suspension plate, wherein a flowing chamber is formed between the gas-injection plate and the bottom surface of the gas-guiding-component loading region, and at least one vacant space is formed among the plurality of connecting components and the suspension plate;
 a chamber frame carried and stacked on the suspension plate;
 an actuator element carried and stacked on the chamber frame for being driven in response to an applied voltage to undergo the bending deformation in a reciprocating manner;
 an insulation frame carried and stacked on the actuator element; and
 a conductive frame carried and stacked on the insulation frame,
 wherein a resonance chamber is formed among the actuator element, the chamber frame and the suspension plate, wherein when the actuator element is enabled to drive the gas-injection plate to move in resonance, the suspension plate of the gas-injection plate is driven to generate the bending deformation in a reciprocating manner, the gas is inhaled through the vacant space, flows into the flowing chamber, and is discharged out, so as to achieve gas transportation.

2. The health monitoring device according to claim 1, wherein the health monitoring device is one selected from the group consisting of a sphygmomanometer, a smart watch, a smart bracelet, a weight scale, a thermometer and a sleep detection device.

3. The health monitoring device according to claim 1, wherein the at least one sensor of the gas detection module comprises a particulate sensor, and the gas detection module further comprises:
 a base comprising:
 a first surface;
 a second surface opposite to the first surface;
 a laser loading region hollowed out from the first surface to the second surface;
 a gas-inlet groove concavely formed from the second surface and disposed adjacent to the laser loading region, wherein the gas-inlet groove comprises a gas-inlet and two lateral walls, the gas-inlet is in communication with an environment outside the base, and two transparent windows are opened on the two lateral walls and are in communication with the laser loading region;
 a gas-guiding-component loading region concavely formed from the second surface and in communication with the gas-inlet groove, wherein a ventilation hole penetrates a bottom surface of the gas-guiding-component loading region; and
 a gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;
 a driving circuit board covering and attached to the second surface of the base;
 a laser component positioned and disposed on the driving circuit board, electrically connected to the driving circuit board, and accommodated in the laser loading region, wherein a light beam path emitted from the laser component passes through the transparent window and extends in a direction perpendicular to the gas-inlet groove, thereby forming an orthogonal direction with the gas-inlet groove;
 an outer cover covering the first surface of the base and comprising a side plate, wherein the side plate has an inlet opening spatially corresponding to the gas-inlet and an outlet opening spatially corresponding to the gas-outlet, respectively,
 wherein the piezoelectric actuator accommodated in the gas-guiding-component loading region, wherein the particulate sensor is positioned and disposed on the driving circuit board, electrically connected to the driving circuit board, and disposed at an orthogonal position where the gas-inlet groove intersects the light beam path of the laser component in the orthogonal direction, so that suspended particles passing through the gas-inlet groove and irradiated by a projecting light beam emitted from the laser component are detected, wherein the first surface of the base is covered with the outer cover, and the second surface of the base is covered with the driving circuit board, so that an inlet path is collaboratively defined by the gas-inlet groove and the driving circuit board, and an outlet path is collaboratively defined by the gas-outlet groove, the outer cover and the driving circuit board, so that the gas is inhaled from the environment outside the base by the piezoelectric actuator, transported into the inlet path through the inlet opening, and passes through the particulate sensor to detect concentration of the suspended particles contained in the gas, and the gas transported through the piezoelectric actuator is transported out of the outlet path through the ventilation hole and then discharged through the outlet opening.

4. The health monitoring device according to claim 3, wherein the base comprises a light trapping region hollowed out from the first surface to the second surface and spatially corresponding to the laser loading region, wherein the light trapping region comprises a light trapping structure having an oblique cone surface and spatially corresponding to the light beam path.

5. The health monitoring device according to claim 4, wherein a light trapping distance is maintained between the transparent window and a position where the light trapping structure receives the projecting light beam.

6. The health monitoring device according to claim 5, wherein the light trapping distance is greater than 3 mm.

7. The health monitoring device according to claim 4, wherein the at least one sensor of the gas detection module comprises a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

8. The health monitoring device according to claim 3, wherein the particulate sensor is a PM2.5 sensor.

9. The health monitoring device according to claim 3, wherein the at least one sensor of the gas detection module comprises a first volatile-organic-compound sensor positioned and disposed on the driving circuit board, electrically connected to the driving circuit board, and accommodated in the gas-outlet groove, so as to detect the gas flowing through the outlet path of the gas-outlet groove.

10. The health monitoring device according to claim 1, wherein the actuator element comprises:
- a piezoelectric carrying plate carried and stacked on the chamber frame;
- an adjusting resonance plate carried and stacked on the piezoelectric carrying plate; and
- a piezoelectric plate carried and stacked on the adjusting resonance plate, wherein the piezoelectric plate is configured to drive the piezoelectric carrying plate and the adjusting resonance plate to generate the bending deformation in the reciprocating manner by the applied voltage.

11. The health monitoring device according to claim 1, further comprising a controlling circuit unit, wherein the controlling circuit unit comprises a microprocessor and a communicator, and the gas detection module is electrically connected to the controlling circuit unit, wherein the microprocessor enables the gas detection module to detect and operate by controlling a driving signal of the gas detection module, and converts a detection raw data of the gas detection module into a detection data for storing, wherein the communicator receives the detection data outputted by the microprocessor, and allows the detection data to be externally transmitted to an external device through the communication transmission for storing, so that the external device generates a gas detection information and an alarm.

12. The health monitoring device according to claim 11, wherein the external device is one selected from the group consisting of a cloud system, a portable device and a computer system.

\* \* \* \* \*